US007773723B2

United States Patent
Nord et al.

(10) Patent No.: US 7,773,723 B2
(45) Date of Patent: Aug. 10, 2010

(54) RADIATION TREATMENT TRAJECTORY AND PLANNING METHODS

(75) Inventors: Janne Nord, Espoo (FI); Jarkko Peltola, Tuusula (FI)

(73) Assignee: Varian Medical Systems International AG (CH)

( * ) Notice: Subject to any disclaimer, the term of this patent is extended or adjusted under 35 U.S.C. 154(b) by 0 days.

(21) Appl. No.: 12/201,271

(22) Filed: Aug. 29, 2008

(65) Prior Publication Data

US 2010/0051824 A1    Mar. 4, 2010

Related U.S. Application Data

(63) Continuation of application No. 12/200,639, filed on Aug. 28, 2008.

(51) Int. Cl.
*A61N 5/10* (2006.01)
*H05G 1/00* (2006.01)
(52) U.S. Cl. .......................................... 378/65; 378/210
(58) Field of Classification Search .................. 378/65, 378/210; 600/425–429
See application file for complete search history.

(56) References Cited

U.S. PATENT DOCUMENTS

| | | | |
|---|---|---|---|
| 5,027,818 A * | 7/1991 | Bova et al. ................... | 600/427 |
| 6,661,870 B2 | 12/2003 | Kapatoes | |
| 6,977,987 B2 | 12/2005 | Yamashita | |
| 7,085,347 B2 | 8/2006 | Mihara | |
| 7,188,999 B2 | 3/2007 | Mihara | |
| 2004/0165696 A1* | 8/2004 | Lee ............................. | 378/65 |
| 2006/0039533 A1* | 2/2006 | Weil et al. .................... | 378/65 |
| 2006/0067469 A1* | 3/2006 | Dooley et al. ................ | 378/65 |
| 2008/0002811 A1* | 1/2008 | Allison ........................ | 378/65 |
| 2008/0226030 A1* | 9/2008 | Otto ............................ | 378/65 |
| 2008/0298550 A1* | 12/2008 | Otto ............................ | 378/65 |

OTHER PUBLICATIONS

Bjorn Hardemark; "Direct Machine Parameter Optimization with RayMachine in Pinnacle"; RaySearch White Paper; 2003; 3 pages.
International Search Report mailed on Oct. 22, 2009 for PCT/US09/54807.
Non-Final Office Action dated May 14, 2009 for U.S. Appl. No. 12/200,639.
Final Office Action dated Apr. 26, 2010 for U.S. Appl. No. 12/200,639.

* cited by examiner

*Primary Examiner*—Edward J Glick
*Assistant Examiner*—Anastasia Midkiff
(74) *Attorney, Agent, or Firm*—Vista IP Law Group, LLP.

(57) ABSTRACT

A radiation system includes a radiation source, and a patient support for supporting a patient, the patient support located adjacent to the radiation source such that the radiation source can deliver radiation towards the patient while the patient is supported on the patient support, wherein the patient support and the radiation source are positionable at least partially around a same spatial region. A system for use to determine a treatment plan includes a user interface for allowing a user to define a plurality of control points, a first parameter, and a second parameter, wherein the user interface also allows the user to prescribe which of the first and second parameters is to be optimized, and which of the first and second parameters is to be interpolated.

41 Claims, 13 Drawing Sheets

```
600
0001111222211110000  Fluence map

Can be converted to a leaf sequence

602a ───  ---II-------------    Leaf positions, time step 1
602b ───  --I------I--------    Leaf positions, time step 2
602c ───  -----I--------II--    Leaf positions, time step 3
602d ───  ---------II-------    Leaf positions, time step 4

604a ───  0000000000000000000   Fluence component form leaf positions, time step 1
604b ───  0001111111100000000   Fluence component form leaf positions, time step 2
604c ───  0000000111111110000   Fluence component form leaf positions, time step 3
604d ───  0000000000000000000   Fluence component form leaf positions, time step 4

600 ───   0001111222211110000   Sum of fluence components
```

FIG. 6

RADIATION TREATMENT TRAJECTORY AND PLANNING METHODS

RELATED APPLICATION DATA

This application is a continuation of U.S. patent application Ser. No. 12/200,639, filed on Aug. 28, 2008, the entire disclosure of which is expressly incorporated by reference herein.

FIELD

This application relates generally to radiation therapy, and more specifically, to radiation treatment trajectory.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. During a radiation planning session, radiation treatment planning is performed before treatment radiation is delivered to a patient. This allows an accurate and precise dosage of radiation to be delivered to a patient. Embodiments of methods and systems for determining treatment plans effectively and accurately are described herein. Also, embodiments of treatment systems that use such treatment plans are described herein.

SUMMARY

In accordance with some embodiments, a radiation system includes a radiation source, and a patient support for supporting a patient, the patient support located adjacent to the radiation source such that the radiation source can deliver radiation towards the patient while the patient is supported on the patient support, wherein the patient support and the radiation source are positionable at least partially around a same spatial region.

In accordance with other embodiments, a radiation method includes placing a radiation source at a first gantry angle, delivering a first beam using the radiation source towards a target supported on a support, the first beam is delivered when the radiation source is at the first gantry angle and when the support is located at a first position, placing the radiation source at a second gantry angle, positioning the support at least partially around a spatial region to move the support from the first position to a second position; and delivering a second beam using the radiation source towards the target when the radiation source is at the second gantry angle and when the support is at the second position.

In accordance with other embodiments, a patient support system includes a patient support having a surface for supporting a patient, the patient support having a longitudinal axis, a positioner coupled to the patient support for positioning the patent support, the positioner configured to rotate the patient support about an axis that is parallel to, and spaced away from, the longitudinal axis.

In accordance with other embodiments, a radiation method includes delivering radiation towards a target using a radiation source, rotating the radiation source at least partially about the target, translating the target towards a first direction, and translating the target towards a second direction that is opposite to the first direction.

In accordance with other embodiments, a radiation method includes delivering radiation towards a target using a radiation source, rotating the radiation source about a first axis to move the radiation source at least partially around the target, and rotating the radiation source in a first direction about a second axis, and rotating the radiation source in a second direction about the second axis.

In accordance with other embodiments, a method of determining a treatment plan includes determining a machine parameter, using an optimization technique to determine a first value for the machine parameter, the first value representing a first condition of a machine to be achieved during a treatment, and using interpolation to prescribe a second condition of the machine to be achieved during the treatment.

In accordance with other embodiments, a system for use to determine a treatment plan includes a user interface for allowing a user to define a plurality of control points, a first parameter, and a second parameter, wherein the user interface also allows the user to prescribe which of the first and second parameters is to be optimized, and which of the first and second parameters is to be interpolated.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings am not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 6 illustrates an example of converting fluence map into leaf sequencing;

DESCRIPTION OF THE EMBODIMENTS

Figure 1:
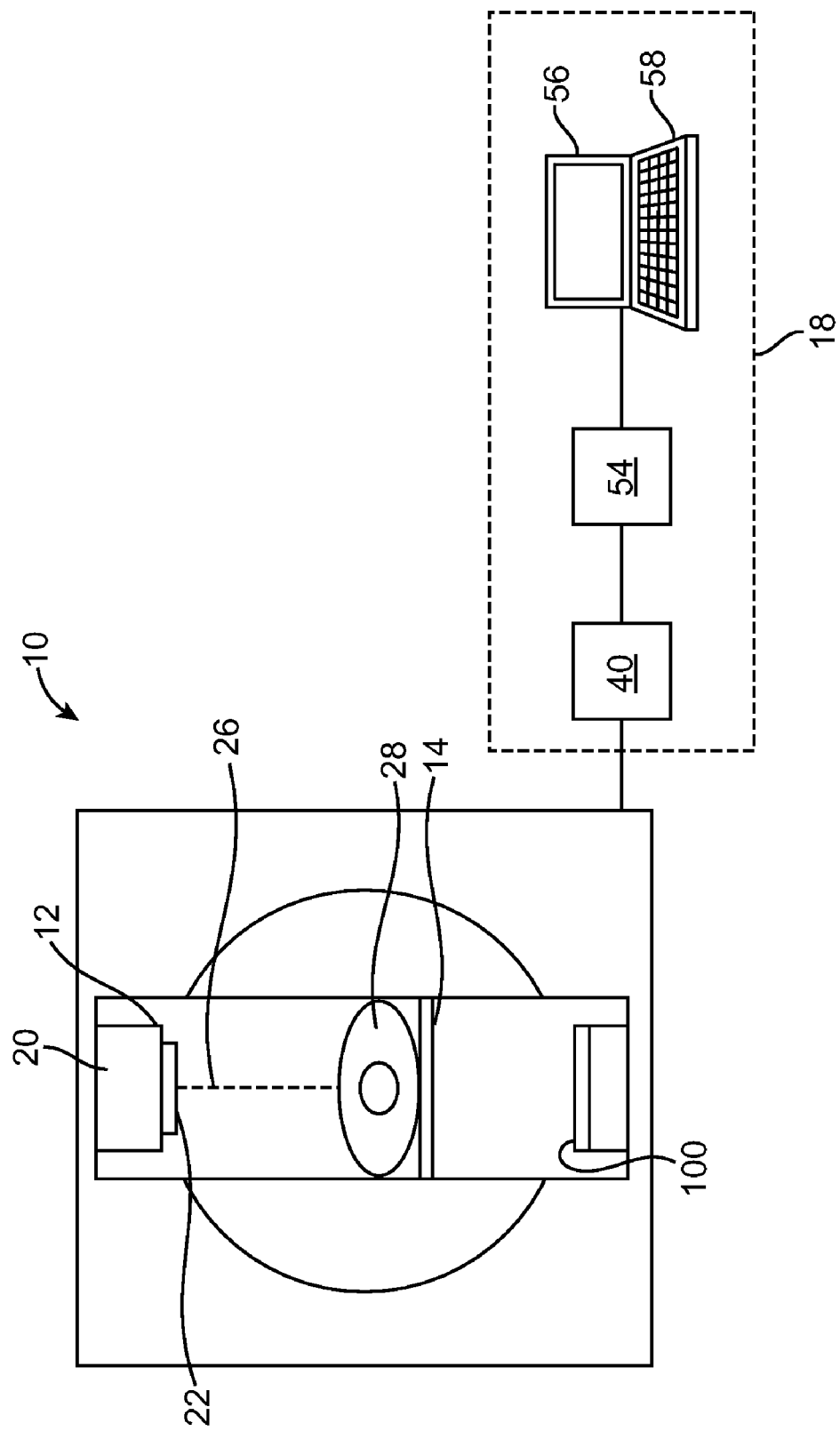
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rote about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
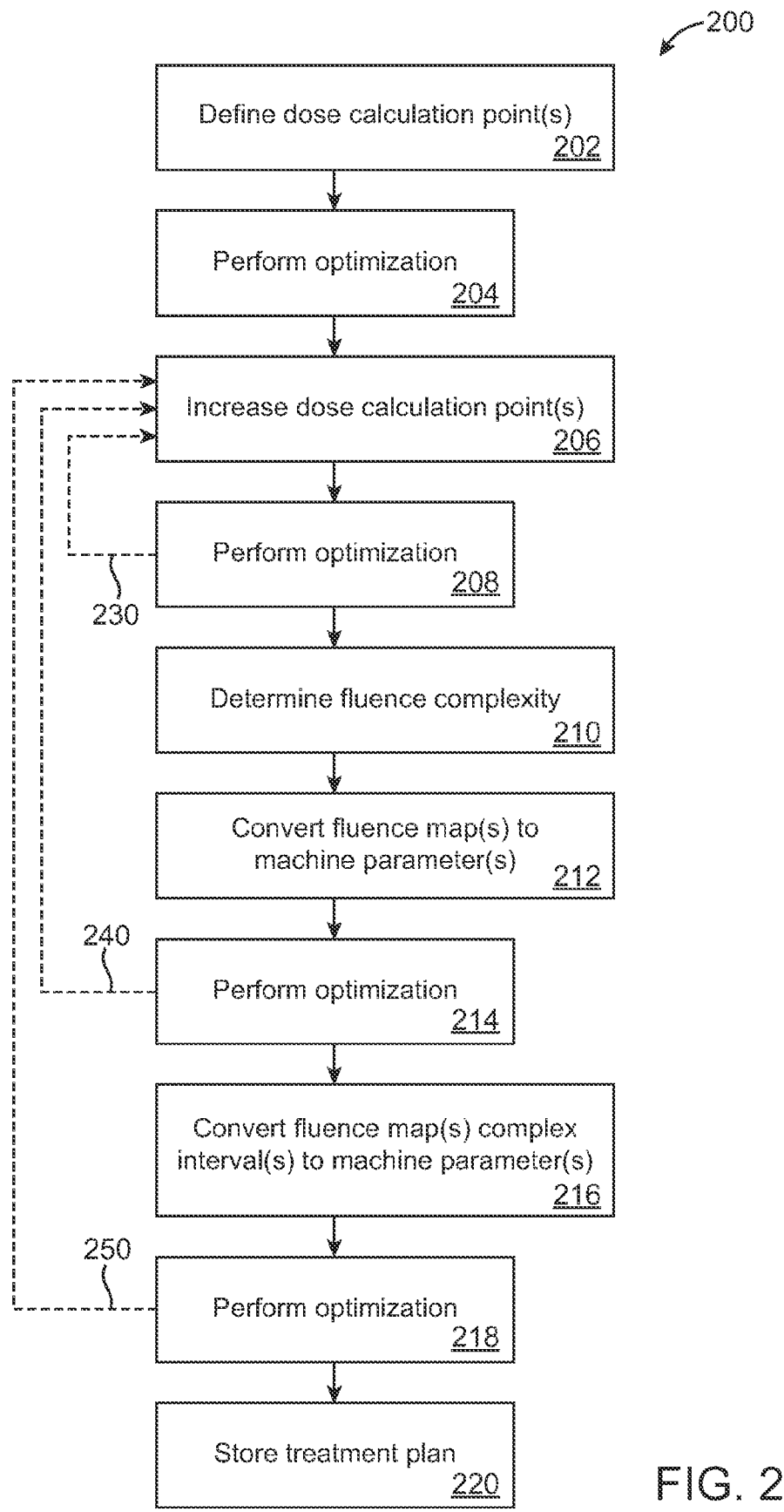
FIGS. 2 and 3 illustrate a method of determining a treatment plan in accordance with some embodiments.
Figure 3:
Figure 4:
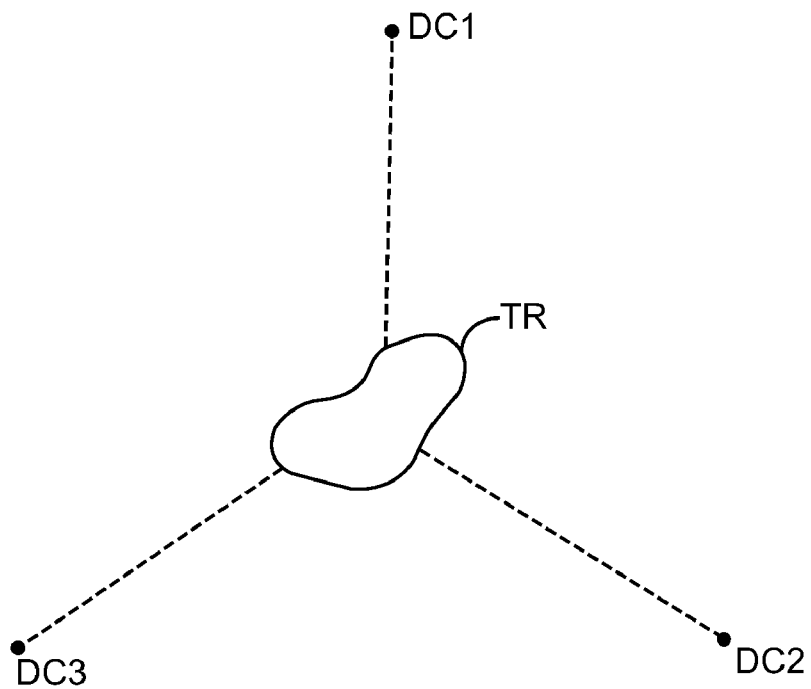
FIG. 4 illustrates an example of a target region and three dose calculation points.

FIGS. 2 and 3 illustrate a method 200 of determining a radiation treatment plan that may be used by the system 10 in accordance with some embodiments. The method 200 will be described with reference to treating a target region TR using a radiation source 20 that rotates about the target region TR (e.g., 360° about the target region TR), as in an arc therapy (FIG. 4). However, it should be understood that the method 200 is not limited to the example illustrated in FIG. 4, and that the method 200 may be used to determine other treatment plans with a different setup. For example, in other embodiments, the method 200 may be used to determine a treatment plan in which the radiation source 20 does not rotate completely about the TR, but only partially (e.g., less than 360° about the patient 28).

First, a number of dose calculation points are defined (step 202). A dose calculation point is used to represent a component that is a part of a divided treatment. In particular, the total dose of a treatment may be divided into components. A broadly defined dose calculation point contains the dose delivered during some part of the treatment. The sum of doses from all dose calculation points is the total dose of the treatment. The division of the treatment into components may be done with respect to various parameters in different embodiments. In the illustrated example, the treatment is initially divided into three components represented by dose calculation points DC1, DC2, DC3, wherein the division is done with respect to the gantry angles such that DC1, DC2, DC3 represent respective 120° gantry ranges (FIG. 4). Division of a treatment based on gantry angles may be useful in determining treatment plans for arc treatments. In other embodiments, the number of dose calculation points may be different from three. For example a 360° treatment can be divided into 10° components, in which case, the number of dose calculation points would be 36. Each component would cover the dose delivered in different 10° gantry angle intervals. In further embodiments, instead of having each dose calculation point representing an interval with a same range, the dose calculation points may represent respective intervals with different ranges (e.g., DC1 may represent gantry angles from 0°-180°, DC2 may represent gantry angles from 180°-300°, and DC3 may represent gantry angles from 300°-360°).

In the illustrated embodiments, for each of the dose calculation points, the radiation can be modeled by assuming radiation coming from one fixed gantry angle. For example, for the dose calculation point covering dose from 0° to 120°, the dose can be calculated by assuming that all radiation in this 0° to 120° interval is coming from 60° angle. It is easier and faster to calculate the dose from a single fixed ganty angle than from a curved path from 0° to 120°.

Figure 5:
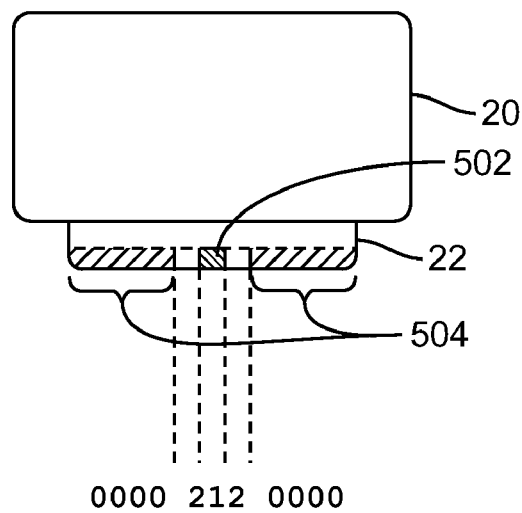
FIG. 5 illustrates an example of a fluence map representing fluence generated using a collimator.

For each of the dose calculation points, the radiation that is desired to be delivered is modeled by considering fluence. Fluence is the amount of radiation passing through a spatial region, and may be represented by a fluence map. A fluence map is a matrix that covers a spatial region (e.g., a plane). For each point in the plane, the fluence map defines the amount of radiation passing through that element. FIG. 5 illustrates an example of a fluence map. In the example, the radiation source sends radiation with strength 2. There is a block 502 (which may be, for example, a leaf of a collimator) in the middle of radiation beam blocking half of the radiation passing through that block. For example, the 502 block may be extended half way to allow radiation to pass through half of a prescribed region. Alternatively, the block 502 may be retracted to let radiation pass through the region half the time, and may be dosed completely to prevent radiation from passing through the region the other half the time. The fluence in the fluence plane is 0 in parts where the collimator leaves 504 block the radiation to prevent the radiation from passing through. The fluence is 2 where all the radiation from source reaches (and passes through) fluence plane. The fluence is 1 where half of the radiation was blocked by the 502 block. The matrix of fluence elements form a fluence map 00002120000.

In some cases, a computer user interface, such as a screen and an input device, may be provided for allowing a user to input data for defining dose calculation points. For example, the screen may display one or more input fields for allowing the user to input the data, such as number of dose calculation points, and treatment division parameters. The screen may also display input fields for allowing user to input target region size, target region shape, maximum allowable dose, minimum required dose, etc. The displaying of the input fields may be done in response to a processor (which may be the same processor 54, or a separate processor) and/or software executing a set of instruction. In such cases, the processor and/or the software determines the dose calculation points by receiving input by the user.

Returning to FIG. 2, next, the processor and/or the software performs optimization using the three defined dose calculation points DC1, DC2, DC3 (Step 204). As discussed, the regions represented by respective dose calculation points DC1, DC2, DC3 are modeled with respective fluence maps. In step 204, the processor and/or software runs the fluence optimization for some number of iterations (e.g., 100). The objective of the optimization is to get fluence maps that produce best dose in patient 28 by optimizing the individual components in the fluence maps. In some cases, the optimization objective may be defined using DVH (dose volume histogram) constraints in patient dose. Dose volume histogram is a graph (function) DVH(x) that tells which fraction of a defined volume receives less than x dose, and DVH constraint is a constraint that describes which shapes of DVH are preferred. For example, a user may specify (e.g., using a user interface) not to put more than 30 Gy dose to spine, but to keep the dose in target between 60 and 70 Gy. The objective is to find out the best fluence map configuration at the various dose points that will give the desired dose at the target, while minimizing dose to healthy tissue outside the target DVH function and constraints am well known in the art.

Next, the method moves to dose calculation point level 2, in which the interval for each dose calculation point is halved such that the treatment is modeled in six intervals (Step 206). The division can be done by assuming that two adjacent dose calculation points at level 2 have the same fluence as the parent fluence map at level 1. So the dose calculation points DC1 and DC2 at level 2 would have a fluence map that is equal to the fluence map of dose calculation point DC1 at level 1 times 0.5. As a result of Step 206, six dose calculation points are modeled with six fluence maps.

Next, the processor and/or the software runs a number (e.g., 100) of iterations of fluence optimization again, this time using the dose calculation points DC1-DC6 at level 2 (Step 208). The objective of the optimization is to get fluence maps that produce best dose in patient 28 by optimizing the individual components in the fluence maps for the six dose calculation points DC1-DC6. The technique for performing the optimization in step 208 may be the same as that described with reference to step 204.

The complexity of all fluences at level 2 is then evaluated (Step 210). Various techniques may be used to evaluate the complexity of a fluence at any given level. In some embodiments, the complexity of a fluence is represented by the complexity of its corresponding fluence map. In such cases, the complexity of the fluence map is calculated by converting the fluence map to machine parameters, and calculating the time required to move the leaves based on the machine parameters. The more the time that is required to move the leaves to achieve a fluence profile, the more complex is the fluence. In other embodiments, instead of, or in addition to, using the time required to move the leaves to determine a complexity of a fluence, other parameters may also be used. For example, in other embodiments, the number of leaves that need to be moved in order to achieve a fluence may also be used to determine the complexity of the fluence. In such cases, the more the number of leaves that need to be moved, the more the complex the fluence. In further embodiments, the distance that the leaf(s) need to travel may also be used to determine the complexity of the fluence. In such cases, the more the distance, the more the complex the fluence. In other embodiments, any combination of the above parameters and/or other parameters not described herein may be used to determine a complexity of a fluence.

Next, the processor and/or the software converts all but the most complex fluence to machine parameters by using a leaf sequencing algorithm (Step 212). FIG. 6 illustrates an example of converting a fluence map 600 to machine parameters using a leaf sequencing technique. As shown in the figure, the fluence represented by the fluence map 600 can be converted to leaf sequence (an example of machine parameters), which in the example, has four leaf positions 602a-602d at respective four time points t=1, 2, 3, 4. In particular, the leaves would first be closed 602a at time step 1. Then the leaves would be open in the regions shown in the leaf configuration 602b at time step 2. Then the leaves would be open in the regions shown in the leaf configuration 602c at time step 3. Then the leaves would be closed again 602d (time step 6). The fluence components 604a-604d for the respective leaf positions 602a-602d are also shown. As shown in the figure, the sum of the fluence components 604a-604 d equals the fluence map 600. In the illustrated example, the most complex region is in the dose calculation point 5 at level 2 (FIG. 3). Thus, the processor and/or software converts all of the fluence to machine parameters, except that for dose calculation point 5. In some cases, the processor and/or software determines whether a level of complexity of a fluence is below a prescribed threshold, and converts the corresponding fluence map to one or more machine parameters for the dose calculation point when it determines that the level of complexity is below the prescribed threshold. In other embodiments, the processor and/or software determines whether a level of complexity of a fluence is above a prescribed threshold, and converts the corresponding fluence map to one or more machine parameters for the dose calculation point when it determines that the level of complexity is above the prescribed threshold.

In the above example, each of the leaf positions 602a-602d is a machine parameter that corresponds with a machine control point. As used in this application, the term "machine control point" or "control point" refers to a component of a treatment plan that includes one or more machine parameters for prescribing a part of the treatment plan. For example, a treatment plan may be prescribed using N number of machine control points, each of which contains machine parameter(s) (such as any or a combination of: gantry speed, gantry angle, beam-on/activation signal, beam-off/deactivation signal, collimator position, leaves' positions, couch position, beam energy, beam type, dose (or monitor units), and dose rate (or beam intensity)) for defining a part of the treatment plan. The number of machine control points that correspond with a fluence map may vary. For example, a complex fluence map may be converted into a higher number of leaves' positions (machine control points), while a simpler fluence map may only require fewer machine control points to achieve the desired fluence. In some cases, the total number of machine control points in a complete treatment plan may be in the range of hundreds or even thousands. In the illustrated embodiments, the number of machine control points are higher than the number of dose calculation points. However, the dose at the dose calculation point is used to evaluate the machine parameters, thereby obviating the need to calculate dose for each of the machine control points, which in some cases, may take up a significant amount of computation time and resources. It has been discovered that determining dose at dose calculation points without doing the same at all of the machine control points can achieve a treatment plan that is sufficiently accurate.

Figure 7:
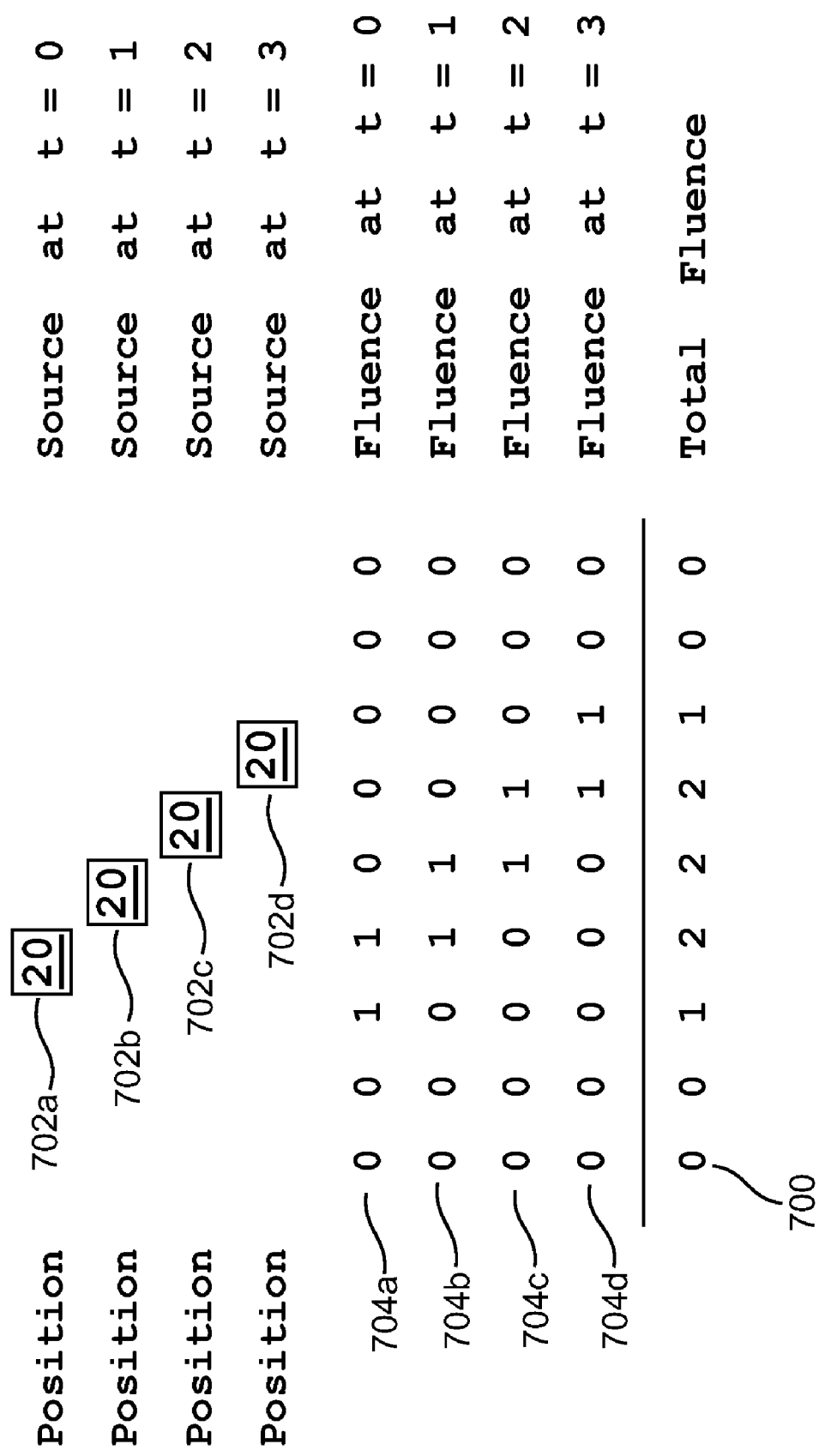
FIG. 7 illustrates an example of converting fluence map into radiation source positioning.

It should be noted that a machine control point may be modeled with other parameters instead of, or in addition to, leaf sequencing. FIG. 7 illustrates an example of converting a fluence map 700 to machine parameters using a leaf sequencing technique. As shown in the figure, the fluence represented by the fluence map 700 can be converted to radiation source positions (another example of machine parameters), which in the example, has four radiation source positions 702a-702d at respective four time points. In particular, the radiation source would first be placed at positions 702a-702d at respective time steps 1-4. The fluence components 704a-704d for the respective radiation source positions 702a-702d are also shown. As shown in the figure, the sum of the fluence components 704a-704d equals the fluence map 700. In the illustrated example, each of the radiation source positions 702a-702d corresponds with a machine control point. Thus, in the example, there are four machine control points that correspond with the fluence map at the corresponding dose calculation point. The number of machine control points that correspond with a fluence map may vary. For example, a complex fluence map may be converted into a higher number of radiation source positions (machine control points), while a simpler fluence map may only require fewer machine control points to achieve the desired fluence. In the above example, the radiation source is illustrated as translating. However, the same principle can be used with a radiation source 20 that rotates, with each time step corresponding to one machine control point.

In the above embodiments, the number of machine control points for each dose calculation point is constant. In other embodiment, the number of machine control points may be different for different dose calculation points, depending on the complexity of the fluence for the particular dose calculation point. Regardless of the number of machine control points, the dose calculation is always performed at the dose calculation points. There will be some error because the angle changes during rotation, but the error could be acceptable if the separation of final dose calculation points is small enough. For example there could be one dose calculation points every 1 or 2 degrees, but within that 1 or 2 degree range, there could be 1, 2, 3, 10, or 100 machine control points. It would be a waste of computation time to calculate the dose with 1/100 degree interval, because that level of accuracy is not required. The change in fluence may be significant due to leaf movement, but the change due to angular rotation may be too small to justify calculating dose at every machine control point.

Returning to FIG. 2, the optimization is continued (Step 214). In particular, gradient back projection technique is used in the optimization for fluence maps, and direct aperture method is used in the optimization for regions modeled with machine control points. In gradient back projection method, the derivatives of the objective function with respect to change in fluence are calculated in gradient map. It is called gradient back projection because the gradients are calculated in some volume elements, and the derivatives of the objective function at those volume elements are projected back and summed to fluence plane to form a gradient plane. Then the fluence is modified by adding the gradient plane to fluence plane (first the gradient plane values are multiplied by some scalar, because the scale is different). Direct aperture methods refer to directly modeling the treatment in machine parameters, wherein the gradient of objective function is calculated with respect to machine parameters and the machine parameters are changed according to the gradients. Thus, in gradient back projection technique, the objective function gradient is calculated with respect to the fluence sum elements, and in direct aperture technique, the objective function gradient is calculated with respect to leaf positions (FIG. 6). In the illustrated embodiments, the dose is still calculated at dose calculation points. The average fluence from machine control points is accumulated at dose calculation point, and the dose is assumed to come from the dose calculation point. The optimization objective of the optimization in step 214 is the same as that described previously. In particular, the machine control points are modified so that they produce a desired fluence in the corresponding dose calculation point (which may represents a range of gantry angles for positions of the radiation source). The goal is to produce an optimal radiation fluence.

In some embodiments, the optimization in step 214 utilizes an iterative technique in which more and more dose calculation points are progressively converted into machine parameters as the number of iterations increases. Alternatively, the process 200 may repeat the step of converting fluence to machine parameters (Step 212) and the step of optimization (Step 214) until all of the dose calculation points (except the ones with the most complex fluence) modeled with fluence maps are converted to machine parameters at machine control points. The determined machine parameters are based on the complexity of fluence from other directions. Therefore the more demanding leaf movements have been considered, except for the range 240-300 corresponding with dose calculation point 5 at level 2 (FIG. 3). For this range, because there is limited time to move leaves to achieve a complex fluence, the resulting fluence may only be partially accomplished. In order to address this, for this range which has been determined to have the most complex fluence, the processor and/or software uses a slower gantry rotation to determine the portion of the treatment that corresponds with this gantry range. With slower gantry rotation, there is more time to move the leaves and the more complex fluence can be converted to machine parameters more accurately (Step 216). In other embodiments, in addition to prescribing a slower gantry speed, the processor and/or software can also use more control points (e.g., more machine control points and/or more dose calculation points) for the complex region(s). Such technique will also allow the more complex fluence to be accomplished more accurately. Also, in other embodiments, different maximum speeds of gantry rotation may be prescribed for different gantry ranges/intervals. In such cases, the machine parameters are determined for the corresponding control points based on the prescribed maximum speed for the corresponding gantry range/interval.

After all of the fluence has been converted to machine parameters at machine control points, the processor and/or software performs optimization again using the machine parameters for all of the dose calculation points (Step 218). The objective of this optimization is to fine tune the previously determined machine parameters such that they produce the desired fluence at the various dose calculation points. The resulting machine parameters for the machine control points are then stored as a treatment plan in a medium for later use (Step 220).

In some embodiments, the method 200 may go one level further, e.g., to level 3, where dose calculation points are increased such that the dose calculation points and machine control points could coincide, but this is not always necessary. This is because the treatment is modeled using final accuracy of machine control points inside the dose calculation point and keeping the machine control points valid (so that the machine would be able to deliver the treatment as presented in machine control points). However, the dose is not calculated from the direction of all machine control points. The total radiation fluence from all of the machine control points belonging to one dose calculation points is first calculated (this is a fast step). Then the dose in patient is calculated from the fluence map in control point. Therefore the part of the treatment modeled as machine control points is a valid treatment. The division to even more dose calculation points is done to decrease another source of error in dose calculation. Large angular separation between dose calculation points may also produce error in dose calculation. Thus, it is desirable that there be enough dose calculation points at final level to have good enough angular dose calculation accuracy, but that number can be smaller that the required number of machine control points. In other embodiments, it could also be same.

So even when the treatment in dose calculation point is modeled as machine parameters, the fluence of a treatment resulting from those machine control points is first calculated and the dose in patient is calculated from that fluence. Maintaining the delivery information in machine control points accounts for machine limitation, such as leaf speed and geometry. On the other hand, when the delivery in dose calculation point is modeled as a fluence only, it ignores most of the machine limitations. The unconstrained optimization is faster and less sensitive to local minima.

In the above embodiments, the processor and/or software evaluates the complexity of fluence in order to determine which control points to change in an iteration, and the conversion starts from most simple interval. Such technique allows the simpler parts of the treatment plan to be determined early on. In other embodiments, the conversion may be based on a different technique. For example, in other embodiments, the conversion may start from most complex interval. Such technique would allow the optimizer to determine the most difficult conversion problems early on in the optimization process. In other embodiments, instead of determining control points to convert based on complexity, all of the control points may be converted regardless of the fluence complexity. In further embodiments, the processor and/or software may use spatial order. For example, control points in first range of angles 0°-10° may be converted, then control points for angles 10°-20° are converted, and then the control points for angles 20°-30° are converted. This technique removes the connectivity problem of machine parameters.

In the above embodiments, the initial number of dose calculation points is small, and is then increased progressively (e.g., from dose calculation level 1 to dose calculation level 2) as the treatment plan is refined. There are two benefits in having small number of dose calculation points initially. First, the optimization may be accomplished faster because the total dose can be evaluated more quickly using fewer number of dose calculation points. Second, the leaf sequencing may be accomplished easier because there is more time (the treatment time modeled in a dose calculation interval is longer) for the leaves to move to produce the desired fluence. As illustrated above, at some point during the treatment planning phase, the fluence maps are desired to be converted to machine parameters. The conversion is not perfect—i.e., because of machine limitation, some parts of the resulting fluence may be different from that calculated at the dose calculation points. This means that the resulting dose may be different from the optimized one. After the conversion has been done, the optimization can be continued in that interval using direct machine parameter optimization methods. This way the treatment planning can first benefit from quick convergence to a good solution (with less consideration of machine limits), and then can decrease the err resulting from the conversion of fluence maps to machine parameters using direct machine parameter optimization (applying machine limits). As illustrated above, the process could first model all intervals of the treatment using fluence maps. Then one or more of the fluence maps are converted to machine parameters. Optimization is continued, in which fluence optimization is used for intervals modeled by fluence maps, and direct machine parameter optimization is used for intervals that are modeled by machine parameters. The errors resulting from the conversion are decreased very efficiently by other intervals modeled by fluence maps. In such technique, more and more intervals are converted to machine parameters as the optimization progresses. Finally the treatment is modeled by machine parameters.

In some cases, practical solution would be to start with only a few dose calculation points, all modeled by unconstrained fluences. Just before the number of dose calculation points is increased, the fluences are converted to machine control points. Because of the small number of dose calculation points, the time they model is longer and the leaf sequencing is easier. Then, to decrease the dose calculation error produced by angular separation, the number of dose calculation points is increased. However, it may be desirable to perform the transition from unconstrained fluences to machine control points in early phase due to easier leaf sequencing.

In other embodiments, instead of having two dose calculation point levels before step 212, the method 200 may include additional dose calculation point level(s). Also, in other embodiments, the dose calculation points may increase at any part of the method 200. For example, the method 200 can repeat steps 206, 208 to increase dose calculation points and perform optimization at any time during the method 200 (See arrows 230, 240, 250 in FIG. 2). In further embodiments, the method 200 may include only one dose calculation point level. In such cases, steps 206, 208 may be omitted. Also, in other embodiments, instead of increasing dose calculation points by subdividing the intervals for all of the dose calculation points, only the intervals for a subset of all the dose calculation points are subdivided to increase the number of dose calculation points. In any of the embodiments described herein, the optimization used by the method 200 is an iterative technique, in which cases, the number of dose calculation points may be increased at any one of the iterations.

In the above embodiments, the process 200 initially models parts of a treatment (e.g., an arc treatment) in 120° intervals of gantry angles with fluence maps. In other embodiments, the treatment may be modeled in other intervals (e.g., 1°, 5°, 10°, etc.) of gantry angles. Also, in other embodiments, the treatment may be modeled initially using fluence maps for some intervals, and machine parameters (e.g., leaf positions) for other intervals. For example, in other embodiments, the treatment may be divided into components, for example in 10 degree intervals in gantry angle, in which the first three intervals may be modeled by fluence maps and the rest of 33 intervals with direct machine parameters. Both modeling techniques to present part(s) of treatment have their advantages. A fluence map can very efficiently represent radiation from some direction and there are very efficient optimization methods to find good fluence maps. However, in some cases, it may be difficult to model machine limitations with fluence map optimization. On the other hand, if a part of the treatment in an interval is modeled using machine parameters, it is easier to apply machine limitations in optimization. However, these optimization methods may be slower, more constrained, and may be more easily trapping into a local minima.

In the above embodiments, the division of the treatment into components is done with respect to the gantry angles. In other embodiments, the division of the treatment into components may be done with respect to other parameters. For example, in other embodiments, the dose calculation points may be defined so that they correspond with respective time. For example a 60 second treatment can be divided into 6 dose calculation points. First dose calculation point would cover the dose delivered from 0 second to 10 second, second dose calculation point from 10 second to 20 second, and so on.

In other embodiments, the dose calculation points may be defined so that they correspond with monitor units. Monitor units is the amount of radiation units produced by the machine 10. For example a 600 MU treatment may be divided into 3 dose calculation points. First dose calculation point would cover the dose delivered from 0 to 200 MU, second dose calculation point would cover the dose delivered from 200 to 400 MU, and third dose calculation point would cover the dose delivered from 400 to 600 MU.

In other embodiments, the dose calculation points may be defined so that they correspond with respective regions of the patient 28 (e.g., different parts of a target region).

In other embodiments, the dose calculation points may be defined such that they correspond to some other geometric parameters. For example, the dose calculation points may be defined such that they correspond with respective positions of the support 14 (e.g., couch) along its longitudinal axis, with respective angles of the support 14, or respective collimator angles.

Figure 8:
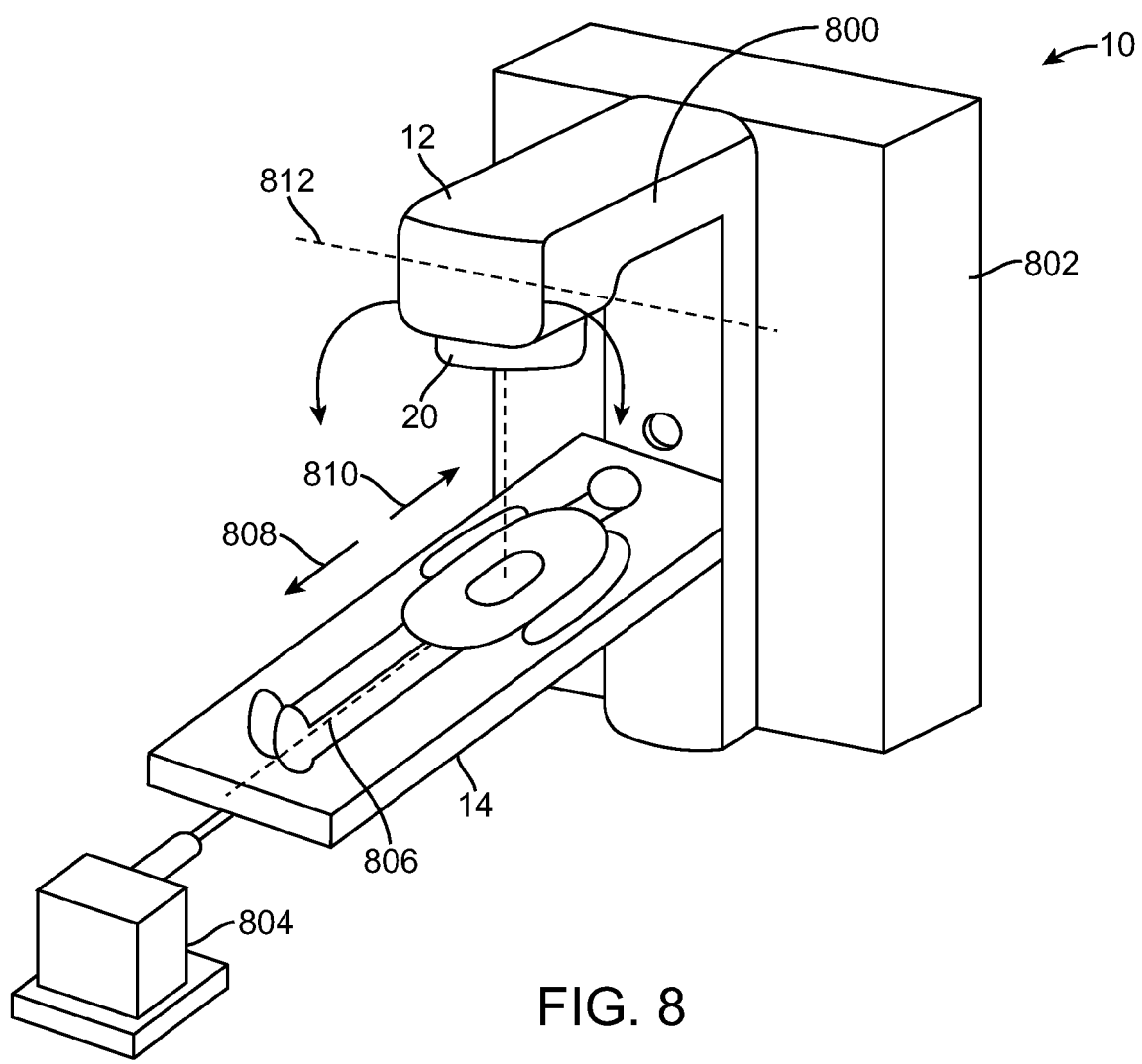
FIG. 8 illustrates a radiation system in accordance with other embodiments.

In the above embodiments, the treatment is described as involving rotating the radiation source 20 at least partially around the patient 28. However, in other embodiments, the treatment may also involve translating the patient 28 relative to the radiation source 20. FIG. 8 illustrates another embodiment of a radiation system 10 in which the patient support 14 is translatable. The system 10 includes a gantry 12 having an arm 800, a support structure 802 to which the gantry is rotatably coupled, and a radiation source 20. In the illustrated embodiments, the patient support 14 is coupled to a positioner 804, which is for translating the patient support 14 in a back and forth manner. During use, the radiation source 20 rotates at least partially around the patient 28 so that radiation can be delivered to target region from a plurality of gantry angles. Also, during use, the positioner 804 moves the patient support 14 along the longitudinal axis 806 (the Z-axis) forward 808 and backward 810, so that different parts of the target region along the axis 806 may receive radiation from a plurality of gantry angles. Thus, by coupling the rotation of the radiation source 20 with the translation of the patient support 14, any part of the target region along the axis 806 may be treated by radiation delivered from a plurality of gantry angles. The system 10 of FIG. 8 is advantageous for treating target that cannot be irradiated with one gantry rotation using existing systems. For examples, the system 10 may be used to perform whole body irradiation or irradiation of long tumor near spine with one continuous radiation trajectory. Also, providing back and forth trajectories is desirable in that it results in control points that represent independent degrees of freedom in the optimization that have independent constraints. In addition, translating the patient support 14 in a back and forth manner during a treatment saves time. The trajectory is simple and easy to understand spatially, and saves treatment planning time. This allows the trajectory to be evaluated easily, and used for many purposes. In some cases, the radiation source 20 may be stationary while the patient support 14 is translated back and forth. This allows radiation to be modulated along the axis 806 such that different parts of the target region along the axis 808 receives different amount of radiation (i.e., for a given gantry angle).

The above described trajectory also allows collision between radiation device and patient 28/support 14 to prevented more easily. This is because in the above described trajectory, the radiation source moves relative to the patient 28 and support 14 in paths that form a cylinder. Cylinder is relatively easy to understand spatially, and therefore, a user may more easily evaluate a risk of collision for such trajectory than for a more complex trajectory. In some embodiments, the system 10 uses a collision prevention mechanism that involves comparing an image of the patient 28 and the support 14 with a cylinder/ring with a specific radius, and checking to see if the cylinder/ring collides with the patient 28 or support 14. Because the support 14 moves back and forth along the same route, the collision detection cylinder will be the same for all passes. This simplifies the collision detection.

In other embodiments, instead of moving the patient support 14, the radiation source 20 may be translatable in the Z-axis direction. In either case, the patient support 14 and the radiation source 20 may be considered as moveable or translatable relative to each other. In further embodiments, the radiation source 20 may be configured to tilt about an axis (e.g., axis 812) that forms an angle (e.g., 90°) relative to the longitudinal axis 806. During use, the radiation source 20 tilts about the axis 812 so that radiation may be delivered to different parts of the target region along the axis 806. The radiation source 20 also rotates at least partially around the patient 28 so that it can deliver radiation to the target region from a plurality of gantry angles.

Figure 9:
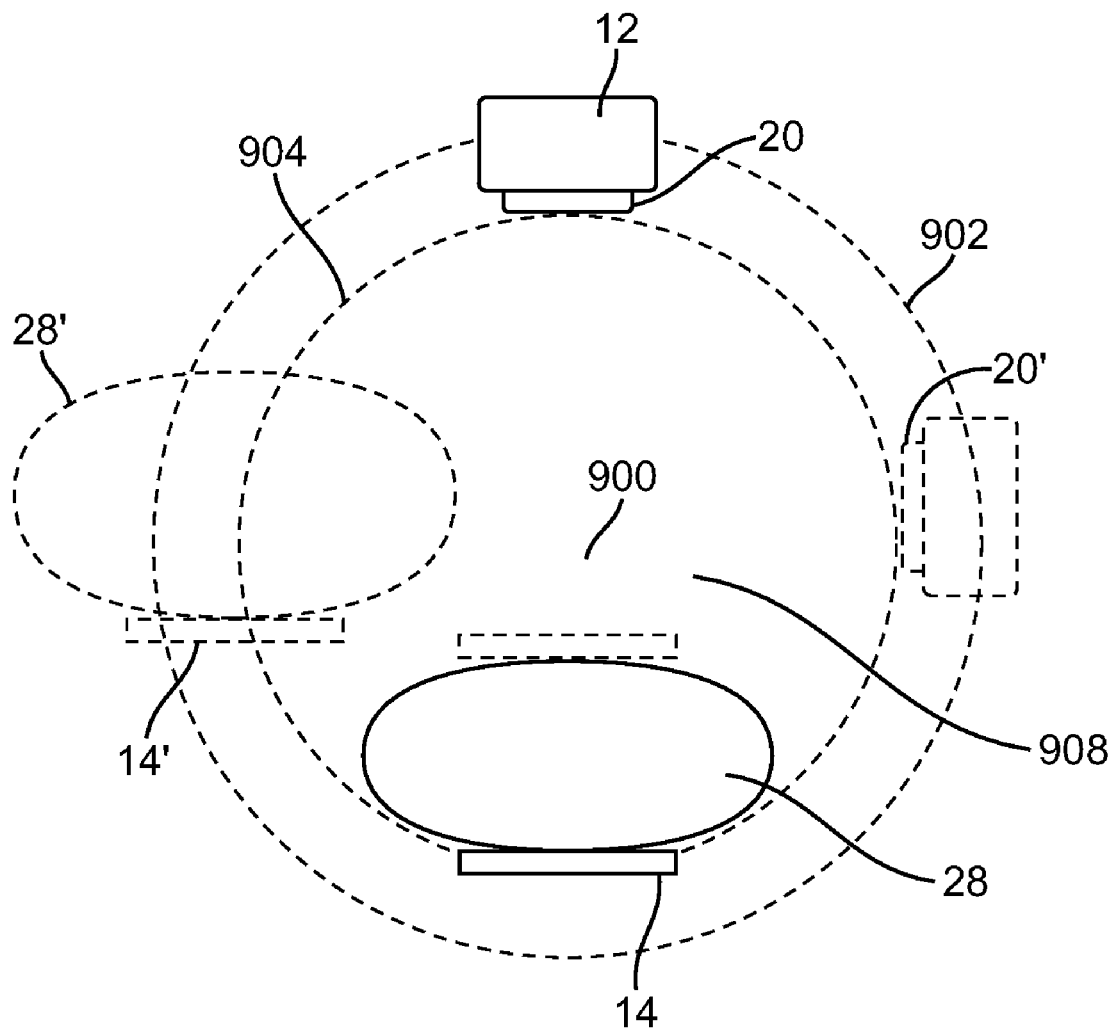
FIG. 9 illustrates another radiation system in accordance with other embodiments.

In other embodiments, the patient support 14 may be configured to rotate during the treatment. FIG. 9 illustrates another embodiment of a radiation system 10 in which the patient support 14 is configured to rotate in correspondence with the rotation of the radiation source 20. In the illustrated embodiments, the patient 28 with the support 14 is shifted away from the isocenter 900. During use, the radiation source 20 rotates at least partially along path 902 to deliver radiation to the patient 28 from a plurality of gantry angles. In correspondence with the position of the radiation source 20, the patient support 14 is configure (e.g., using a positioner) to rotate at least partially along path 904. As shown in the figure, at another point in time during a treatment procedure, the radiation source is moved to another gantry position (represented by reference numeral 20'), and accordingly, the support and the patient are moved around spatial region 908 such that the support and the patient is at operative positions (represented by reference numerals 14', 28') opposite from the radiation source. Such configuration is beneficial in that it provides relatively more room between the patient 28 and the radiation source 20, thereby alloying bigger and heavier patient (which may otherwise be impossible if the support 14 is doser to the isocenter) to be treated. Such feature is also advantageous in that it allows the patient 28 who is being treated to feel more comfortable (especially if the patient 28 is claustrophobic), and reduces the risk of having the patient 28/support 14 collide with the radiation source 20. In the illustrated embodiments, the radiation source 20 and the patient support 14 (with the patient 28) both rotates at least partially around a spatial region 908, and about an axis (which may coincide with, or locate next to, isocenter 900). It should be noted that the term "around" (e.g., as in "around a spatial region") is not limited to movement by the support 14 or source 20 that is in an arc or circular path, and that the term "around" may refer to movement by the support 14 or source 20 that is in other path shapes in different embodiments, as long as the trajectory of the support 14 or source 20 forms a loop that surrounds the spatial region, or a partial loop (e.g., an arc that is less than 360°) that partially surrounds a part of the spatial region. In other embodiments, the radiation source 20 and the patient support 14 (with the patient 28) may rotate about different respective axes that are parallel to, and spaced apart from, each other.

Figure 10:
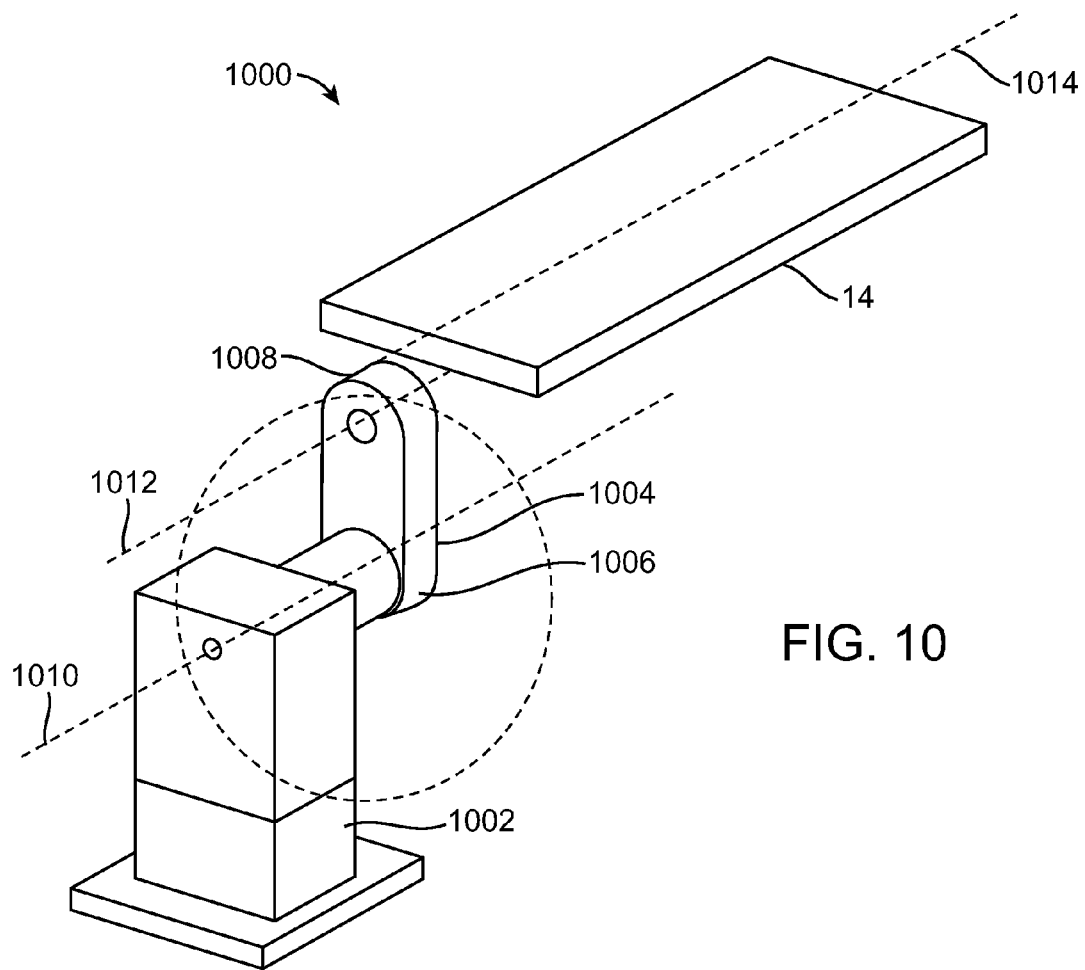
FIG. 10 illustrates a patient support system in accordance with some embodiments.

FIG. 10 illustrates a patient support system 1000 that may be used to move the patient support 14 in the manner described in the embodiment of FIG. 9. The patient support system 1000 includes a base 1002, an arm 1004, and the patient support 14. The arm 1004 has a first end 1006 that is rotatably coupled to the base 1002, and a second end 1008 that is rotatably coupled to the support 14. In particular, the arm 1004 is rotable about an axis 1010 relative to the base 1002, and is also rotatable about another axis 1012 relative to the support 14. During use, a positioning device (e.g., a motor) in the base 1002 rotates the arm 1004. As the arm 1004 rotates about the axis 1010, the support 14 is rotated relative to the arm 1004 about the axis 1012 such that the support surface of the support 14 always faces upward while the support 14 is rotated about the axis 1010. In other embodiments, the patient support system 1000 may further include a positioning device coupled between the support 14 and the arm 1004 for translating the support 14 back and forth along axis 1014. This allows the patient support system 1000 to be used in a similar manner as that described with reference to FIG. 8. It should be noted that the patient support system 1000 is not limited to the configuration described previously, and that the patient support system 1000 may have other configurations (e.g., may have different degrees of freedom) in other embodiments, as long as the patient support 14 can move at least partially around the patient 16.

It should be noted that any of the trajectories described herein (including the trajectory described with reference to FIGS. 8 and 9) may be used in the treatment planning method 200 described with reference to FIG. 2. For example, with respect to the embodiments of FIG. 9, the method 200 may involve defining a parameter that corresponds with rotation of the patient support 14. In such cases, the rotation parameter may be optimized during the method 200 (e.g., in step 204, 208, 214, and/or 218). Similarly, with respect to the embodiment of FIG. 8, the method 200 may involve defining a parameter that corresponds with a translation of the patient support 14. In such cases, the translation parameter may be optimized during the method 200 (e.g., in step 204, 208, 214, and/or 218). As discussed, providing back and forth trajectories is desirable in that it results in control points that represent independent degrees of freedom in the optimization that have independent constraints. As used in this specification, the term "optimization" (or variation thereof—e.g., optimizes, optimizing, etc.) refers to the act of making something better, which may involve changing a value of a parameter, wherein the changing of the value may be performed manually by a user, or automatically using an optimization software.

Figure 11A:
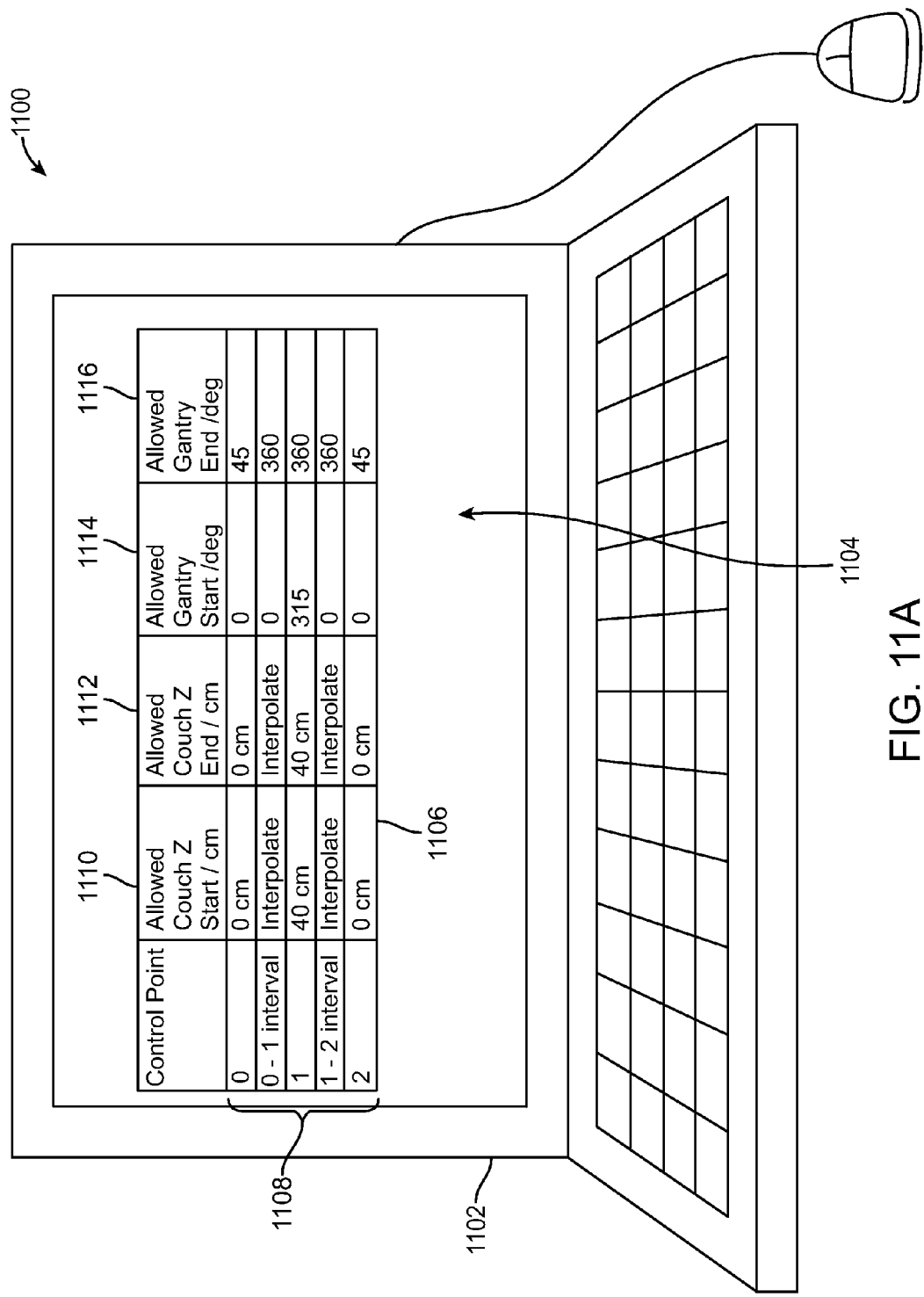
FIGS. 11A-11C illustrate examples of trajectories of a treatment plan.

FIG. 11A illustrates an example of a user interface 1100 that may allow a user to determine a treatment plan in accordance with some embodiments. As used in this specification, the term "user" may refer to a single person, or a plurality of persons. In some cases, the user interface 1100 may be used in the method 200 to determine a treatment plan. The user interface 1100 includes a screen 1102 displaying an input interface 1104. The input interface 1104 may be generated by a processor that executes a set of instruction programmed to provide the image of the input interface 1104. In the illustrated embodiments, the input interface 1104 includes a table 1106 having fields that allow the user to input parameters and/or values. In the illustrated example, the user has defined in table 1106 control points 1108, parameter 1110 for the allowable starting point of support 14, parameter 1112 for allowable ending point of support 14, parameter 1114 for allowable gantry starting angle, and parameter 1116 for allowable gantry ending angle. As shown in the example, a control point may represent a single point (e.g., "0," "1," "2"), or an interval between two points (e.g., "0-1 interval," "1-2 interval"). The table 1106 includes various input fields for allowing the user to input values for the parameters at different control points. As shown in the example, a value may be a numerical value, or an instruction (e.g., "interpolate"—which specifies that values for the corresponding control point are to be calculated in accordance with a prescribed scheme). In some embodiments, the user needs not enter all or any value for the input fields. In such cases, the processor/software for determining the treatment plan is configured to determine the values for the various fields in the table 1106.

In the illustrated example, the trajectory is defined by the control points 108, wherein each control point 108 defines a region in parameter space. The optimized trajectory has to pass through the defined region before proceeding to the next control point 108. The allowed region (range of parameters) between the control points is also defined. Thus, the control points define the region where the machine control points must be placed. In some cases, the processor / software for determining the treatment plan is configured to generate machine control points based on these rules and the defined parameters. For example, as similarly discussed with reference to FIG. 2, the processor/software may perform optimization based on geometric properties of target region(s) and healthy region(s). The processor/software may then continue with the optimization using dose based method(s), e.g., direct aperture method, or fluence based method. In some embodiments, the user interface 1100 allows the user to input initial values for some or all of the parameters. During the optimization process, the processor/software optimizes the values based on certain user-defined constraints (e.g., size, shape, and location of target, path of source, etc.). In other embodiments, the processor/software may be configured to determine the values for the parameters without any initial input values from the user.

In the illustrated example of FIG. 11A, the trajectory would move the support 14 from 0 cm to 40 cm in the Z direction (from control point 0 to control point 1), and back to 0 cm (from control point 1 to control point 2). The gantry 12 would rotate ° from somewhere between 0° and 45° to between 315° and 360°, and back to between 0° and 45°. The Z-positions of the support 14 would be interpolated (e.g., linearly, or using some other interpolation scheme) between the control points. In some embodiments, the optimizer of the processor/software that is used to perform method 200 is configured to determine the route between the control points for gantry angles in the 0° to 360° interval.

Figure 11B:
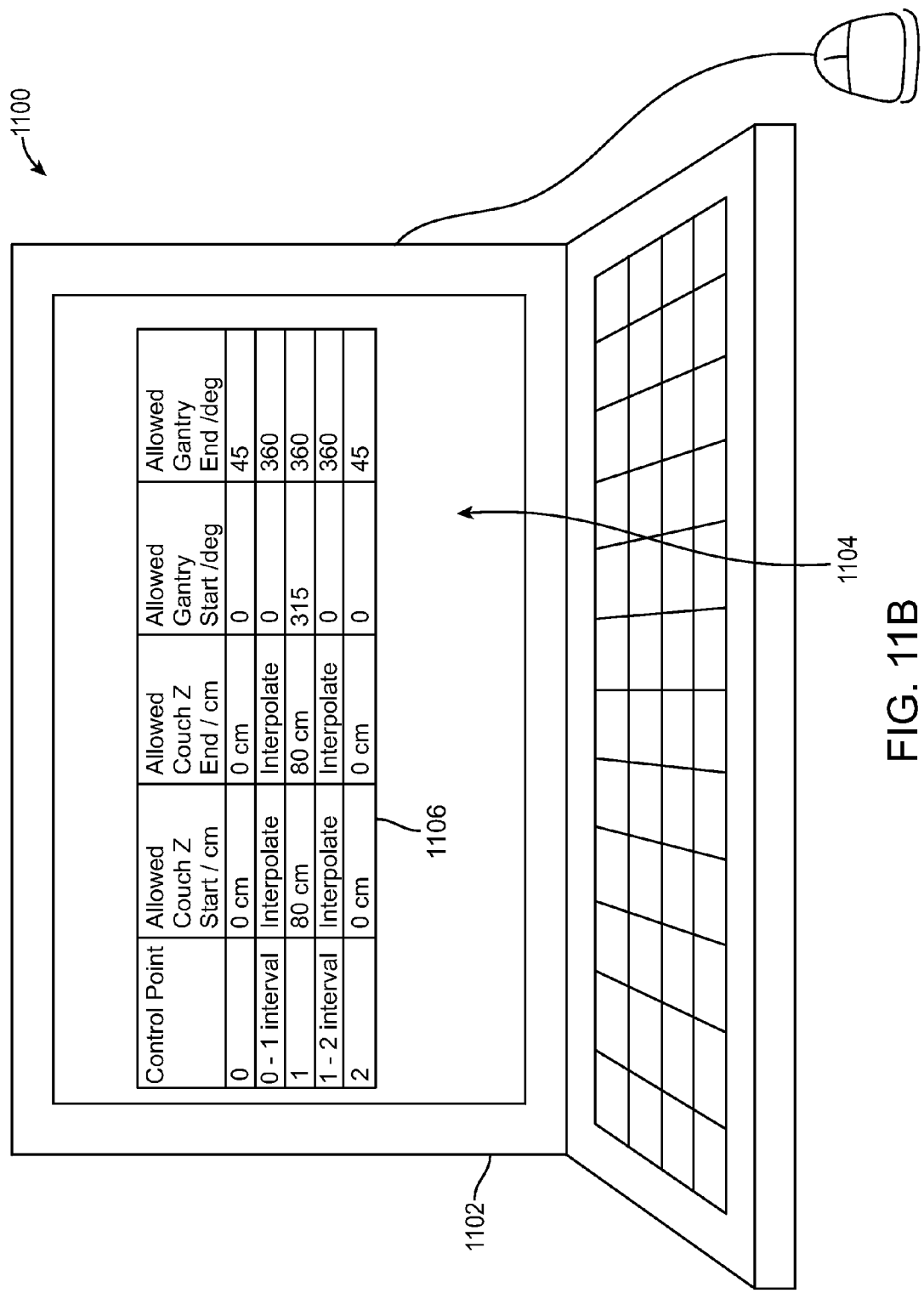
Figure 11C:
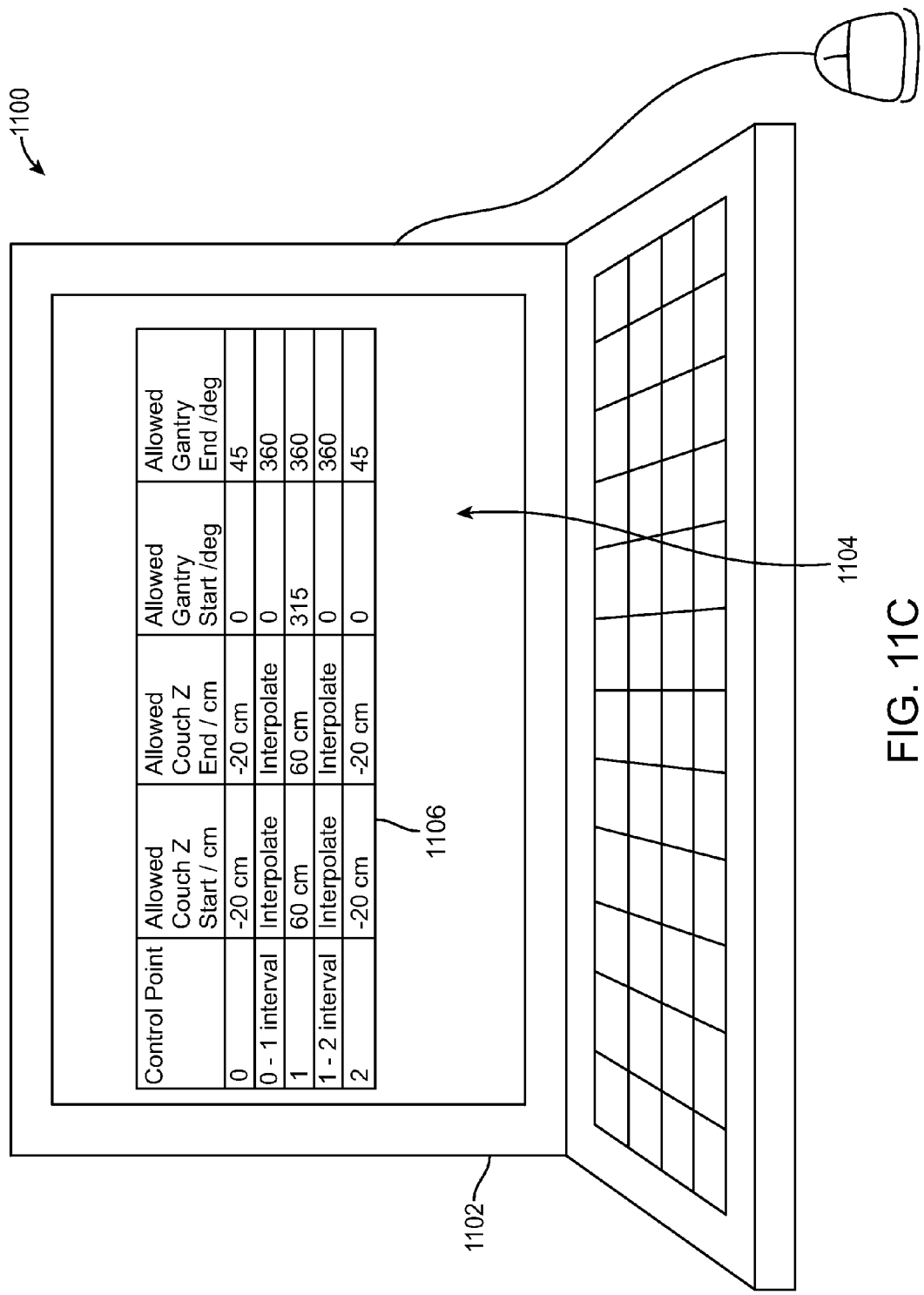

In some cases, the user interface 1100 also allows the user to perform simple operations on defined trajectory. For example, in some embodiments, the trajectory of FIG. 11A may be stretched in the Z-direction by applying a multiplication of 2 in the Z-direction of the support 14. After the multiplication operation, the trajectory would be that shown in FIG. 11B. In other embodiments, at least part of the trajectory may be shifted. For example, the support 14 may be translated in the Z-direction by −20 can from the trajectory of FIG. 11B, which will result in the trajectory of FIG. 11C.

In any of the embodiments described herein, the range of relative motion between the support 14 and the radiation source (or a reference location) can be a value that is between 5 cm and 50 cm. This range is adequate if the target is one connected region. In other embodiments, if the target includes multiple regions (e.g., which may be separated from each other) desired to be treated, then the range of relative motion between the patient support 14 and the radiation source could be anywhere between 5 cm and 2 m.

In some embodiments, the user interface 1100 allows the user to save the designed trajectory in a medium. The trajectory may be saved as a part of a treatment plan, which will be used later in a treatment procedure. Alternatively, or additionally, the trajectory may be saved as a trajectory class. In some cases, the trajectory classes may be organized based on specific machines (e.g., different machines may have different classes of trajectories), patient anatomy, location of target regions, sizes of target regions, shapes of target regions, and/or other disease specific factors. In such cases, a user may retrieve a trajectory from one of the available trajectory classes, based on the specific machine, target region's shape, size, and location, and type of disease. The user may then revise the retrieved trajectory to fine-tune it so that is can be better used for a specific treatment for a specific patient. For example, the user may perform a multiplication and/or an adding procedure for any part (e.g., a parameter type) of the trajectory, such as those discussed with reference to FIGS. 11B and 11C, to thereby fit the dimensions and/or positions of a target in a specific patient.

It should be noted that the type of parameters that may be defined using the user interface 1100 is not limited to the example discussed, and that the user interface 1100 may allow the user to define other parameters, such as gantry angle, positions (e.g., x, y, z) of support 14, orientations ($ø_x$, $ø_y$, $ø_z$) of support 14, dose (e.g., user may specify whether dose is to be delivered for a control point), dose rate, leaves' positions, and speed limits (e.g., of gantry rotation, leaves movements, support 14 movements, etc.).

As illustrated in the above embodiments, the user interface 1100 provides a flexible method for a planner to communicate to the optimizer which class of trajectories is considered for a specific case. The trajectory is defined as a set of control points, in which some parameters are to be optimized, and other parameters are to be interpolated. In some embodiments, parameters that are not optimized are interpolated using an interpolation scheme. The user interface 1100 also allows ranges to be defined, and provides tools for a user to manipulate the trajectory class. In some cases, the parameters to be optimized may be different for different intervals of the treatment. Thus, the user interface 1100 provides a tool for allowing a user to define a trajectory that is flexible enough for different applications, and is easy to converge to a good solution (because not all of the parameters need to be optimized—some of the parameters may be interpolated).

Although the above embodiments have been described with reference to delivering treatment radiation that is in the form of x-rays, in other embodiments, the system and technique described herein may be used for other types of treatment energy. For examples, in other embodiments, in other embodiments, the radiation source 20 may be a proton source for delivering protons to treat a patient, or an electron source for delivering electrons. Accordingly, embodiments of the treatment planning technique described herein may be used to determine treatment plan for other types of treatment, such as proton treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

Computer System Architecture

Figure 12:
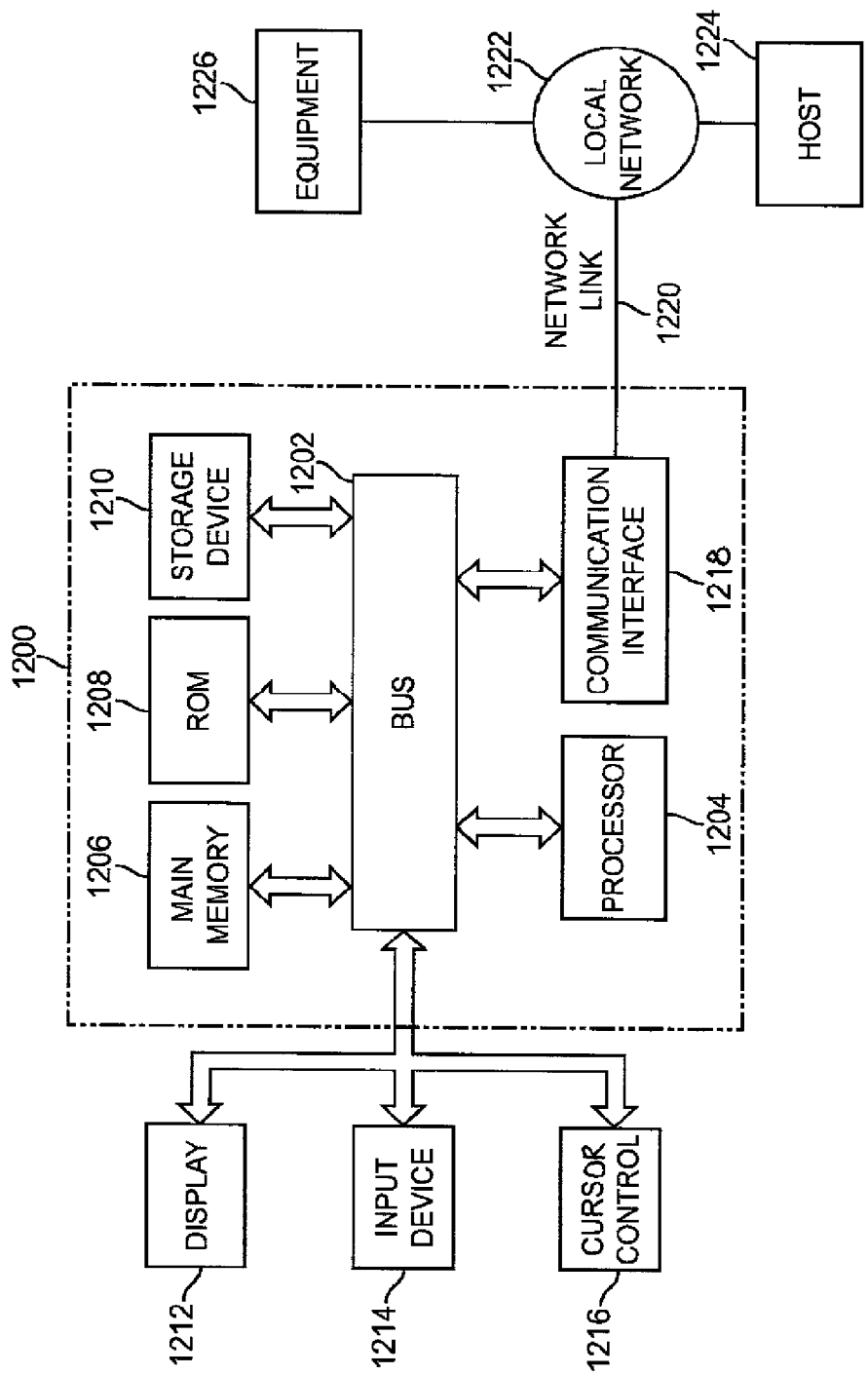
FIG. 12 is a block diagram of a computer system architecture, with which embodiments described herein may be implemented.

FIG. 12 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software. a4

The term "computer-readable medium" as used herein refers to any medium that participates in providing instructions to the processor 1204 for execution. Such a medium may take many forms, including but not limited to, non-volatile media, and volatile media. Non-volatile media includes, for example, optical or magnetic disks, such as the storage device 1210. Volatile media includes dynamic memory, such as the main memory 1206.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. A method of determining a treatment plan, comprising:
   determining a machine parameter;
   using an optimization technique to determine a first value for the machine parameter, the first value representing a first condition of a machine to be achieved during a treatment;
   using interpolation of the machine parameter to prescribe a second condition of the machine to be achieved during the treatment; and
   storing the first value in a computer-readable medium;
   wherein the act of using the optimization technique and the act of using interpolation are performed by a processor.

2. The method of claim 1, further comprising using the optimization technique to determine a second value for the machine parameter, wherein the interpolation is based on the first and second values.

3. The method of claim 1, wherein the machine comprises a radiation treatment machine having a gantry, a radiation source, and a collimator.

4. The method of claim 3, wherein the first condition of the machine comprises a first position of a gantry, a first position of the radiation source, or first position of the collimator.

5. The method of claim 4, wherein the second condition of the machine comprises a second position of a gantry, a second position of the radiation source, or second position of the collimator.

6. The method of claim 1, wherein the second condition is prescribed without optimization of the machine parameter for the second condition.

7. A system for use to determine a treatment plan, comprising:
a user interface for allowing a user to define a plurality of control points for a treatment plan;
wherein the user interface is configured for allowing a user to selectively choose one or both of two available choices for a first machine parameter for one of the control points, said two available choices being optimization and/or interpolation of said first machine parameter in a treatment planning process, and for allowing the user to selectively choose one or both of two available choices for a second machine parameter for the one of the control points, wherein said two available choices includes optimization and interpolation of said second machine parameter in the treatment planning process.

8. The system of claim 7, wherein the plurality of control points correspond with respective time points or intervals.

9. The system of claim 7, wherein the user interface is configured for allowing the user to prescribe whether dose is to be delivered for a time interval that corresponds with one of the control points.

10. The system of claim 7, further comprising a medium for storing the defined control points and the first and second machine parameters as a trajectory class.

11. The system of claim 7, wherein the user interface is configured to allow the user to scale a value for one of the machine parameters using a multiplier.

12. The system of claim 7, wherein the user interface is configured to allow the user to adjust a value for one of the machine parameters by adding a constant value.

13. The system of claim 7, further comprising a processor for performing an optimization for the first or second machine parameter using a geometric evaluation.

14. The system of claim 7, further comprising a processor for performing an optimization for the first or second machine parameter using a dose based method.

15. The system of claim 14, wherein the dose based method comprises a direct aperture method.

16. The system of claim 14, wherein the dose based method comprises a fluence based method.

17. The system of claim 7, wherein one of the first and second machine parameters that is prescribed to be optimized corresponds with one of the control points, and the user interface is configured for allowing the user to define a value for the one of the first and second machine parameters that is prescribed to be optimized.

18. The system of claim 7, wherein the user interface is configured for allowing the user to define a value for an optimizable parameter between two of the control points.

19. The system of claim 18, wherein the optimizable parameter comprises one of the first and second machine parameters that is prescribed to be optimized.

20. The system of claim 7, wherein the user interface comprises a screen for presenting information to the user, and an input device for receiving input from the user.

21. The system of claim 7, wherein the first machine parameter is optimized and the second machine parameter is interpolated, the system further comprising a computer-readable medium for storing the optimized first machine parameter and the interpolated second machine parameter as parts of the treatment plan.

22. A system for use to determine a treatment plan, comprising:
a user interface for allowing a user to define a control point for a treatment plan;
wherein the user interface is configured for allowing the user to selectively choose one or both of two available choices for a machine parameter for the control point, wherein said two available choices includes optimization and interpolation of said machine parameter in a treatment planning process.

23. The system of claim 22, wherein the control point corresponds with a time point or interval.

24. The system of claim 22, wherein the user interface is configured for allowing the user to prescribe whether dose is to be delivered for a time interval that corresponds with the control point.

25. The system of claim 22, further comprising a medium for storing the defined control point and the machine parameter as a trajectory class.

26. The system of claim 22, wherein the user interface is configured to allow the user to scale a value for the machine parameter using a multiplier.

27. The system of claim 22, wherein the user interface is configured to allow the user to adjust a value for the machine parameter by adding a constant value.

28. The system of claim 22, further comprising a processor for performing an optimization of the machine parameter using a geometric evaluation.

29. The system of claim 22, further comprising a processor for performing an optimization of the machine parameter using a dose based method.

30. The system of claim 29, wherein the dose based method comprises a direct aperture method.

31. The system of claim 29, wherein the dose based method comprises a fluence based method.

32. The system of claim 22, wherein the user interface comprises a screen for presenting information to the user, and an input device for receiving input from the user.

33. The method of claim 1, wherein the act of using interpolation to prescribe the second condition of the machine to be achieved during the treatment comprises:
obtaining a first user defined value that represents a first desired machine state;
obtaining a second user defined value that represents a second desired machine state; and
interpolating between the first and second user defined values to obtain one or more interpolated machine states, wherein the one or more interpolated machine states comprise the second condition of the machine to be achieved during the treatment.

34. The method of claim 1, further comprising:
determining a complexity of a fluence; and
changing a control point associated with the machine parameter based at least in part on the complexity of the fluence.

35. The method of claim 1, further comprising:
determining a plurality of control points, one of the plurality of control points corresponding to the machine parameter; and
determining a plurality of dose calculation points, wherein the number of the dose calculation points is less than the number of the control points.

36. The system of claim 7, further comprising a processor configured to perform the interpolation of the first or second machine parameter by:
obtaining a first value that represents a first desired machine state;
obtaining a second value that represents a second desired machine state; and interpolating between the first and second values to obtain one or more interpolated machine states that are to be achieved during a treatment.

37. The system of claim 7, further comprising a processor configured to determine a complexity of a fluence, and change one or more of the plurality of control points based at least in part on the complexity of the fluence.

38. The system of claim 7, wherein the user interface also allows the user to define a plurality of dose calculation points, wherein the number of the dose calculation points is less than the number of the control points.

39. The system of claim 22, wherein the user interface is configured to perform the interpolation of the machine parameter by:
obtaining a first value that represents a first desired machine state;
obtaining a second value that represents a second desired machine state; and
interpolating between the first and second values to obtain one or more interpolated machine states that are to be achieved during a treatment.

40. The system of claim 22, further comprising a processor configured to determine a complexity of a fluence, and change the control point based at least in part on the complexity of the fluence.

41. The system of claim 22, wherein the user interface also allows the user to define additional control points for the treatment plan, and dose calculation points, wherein the number of the dose calculation points is less than the number of the control points.

* * * * *